US00PP32823P3

(12) United States Plant Patent
Mazzardis

(10) Patent No.: US PP32,823 P3
(45) Date of Patent: Feb. 23, 2021

(54) BLUEBERRY PLANT NAMED 'NS 14-7'

(50) Latin Name: ***Vaccinium* hybrid**
Varietal Denomination: NS 14-7

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 16/602,640

(22) Filed: Nov. 12, 2019

(65) Prior Publication Data

US 2020/0170159 P1 May 28, 2020

(30) Foreign Application Priority Data

Nov. 22, 2018 (QZ) ..... PBR 2018/3060

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Randall Danskin, P.S.

(57) ABSTRACT

A new and distinct variety of blueberry plant, which is denominated varietally as 'NS 14-7' is described, with a strong vigor and which produces large fruit, which is medium to high in acidity, under the ecological conditions prevailing in Yanchep, Western Australia.

3 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 14-7'.

CROSS REFERENCE TO RELATED APPLICATIONS

This application claims the benefit of priority under 35 USC § 119 to Community Plant Variety Office (CPVO) Application No. 2018/3060 for Community Plant Variety Rights, filed on Nov. 22, 2018 for a blueberry plant with a variety denomination of 'NS 14-7', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 14-7' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant '8-10' (unpatented), and a pollen parent, blueberry plant 'EB 8-30' (U.S. Plant Pat. No. 25,889, which is herein incorporated by reference in its entirety) during the 2012 growing season.

Prior Varieties. The seed parent '8-10' is characterized principally by a semi-upright growth habit, a strong vigor, an early season first pick date, and further produces large-sized, firm, high sweetness, and medium acidity fruit under the ecological conditions occurring in Yanchep, Western Australia. The seed parent '8-10' is semi-evergreen and produces fruit on one-year old shoots only.

The pollen parent 'EB 8-30', on the other hand, is characterized principally by a semi-upright growth habit, a medium vigor, a very early season first pick date, and further produces medium-to-large-sized, firm, high sweetness, and low acidity fruit under the ecological conditions occurring in Yanchep, Western Australia. The pollen parent 'EB 8-30' is evergreen and produces fruit on one-year old shoots only.

Origin. The seed from the seed parent '8-10' produced approximately 500 plants following cross-pollination. These new plants were then grown at the aforementioned property, and fruit from these new plants was first observed in 2014. A subsequent assessment of these same self-fertile, new plants conducted during the 2014 growing season led to selecting the 'NS 14-7' variety for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2015 growing season led to a conclusion that the 'NS 14-7' variety was a distinct and new variety of blueberry plant found to be true to the original plant. The new variety of blueberry plant was considered to be novel in view of its strong vigor and large fruit, which exhibited medium to high acidity.

Comparisons. In comparison to the seed parent '8-10' under the ecological conditions occurring in Yanchep, Western Australia, the new variety has a comparable vigor. In this regard, the seed parent and the new variety of blueberry plant both have a strong vigor. In addition, the seed parent produces fruit having a fruit size considered to be large as does the new variety of blueberry plant. Further, the seed parent produces fruit considered to exhibit medium acidity. This is in contrast to the fruit of the new variety of blueberry plant, which is considered to exhibit medium to high acidity.

In comparison to the pollen parent 'EB 8-30' under the ecological conditions occurring in Yanchep, Western Australia, the new variety has a noteworthy vigor. In this regard, the pollen parent is considered to have a medium vigor. However, the new variety of blueberry plant has a strong vigor. In addition, the pollen parent produces fruit having a fruit size considered to be medium to large. In contrast, the new variety of blueberry plant produces fruit considered to be large. Further, the pollen parent produces fruit considered to exhibit low acidity. This is in contrast to the fruit of the new variety of blueberry plant, which is considered to exhibit medium to high acidity.

The new variety of blueberry plant is readily distinguishable from the most closely related, known variety, the 'EB 9-2' blueberry plant described in U.S. Plant Pat. No. 28,149, which is herein incorporated by reference in its entirety. In this regard, the closest known variety 'EB 9-2' has a vigor considered to be strong to very strong under the ecological conditions prevailing in Yanchep, Western Australia. In contrast, the new variety of blueberry plant has a vigor considered to be strong. In addition, the closest known variety, produces fruit having a fruit size considered to be large to very large for the species. In contrast, the new variety of blueberry plant produces large fruit. Further, the closest known variety produces fruit having a fruit acidity considered to be low to medium. This is in contrast to the new variety, which produces medium to high acidity fruit.

The comparisons described above are summarized in the table below.

| | 'NS 14-7' | 'EB 9-2' | '8-10' (Seed) | 'EB 8-30' (Pollen) |
|---|---|---|---|---|
| Plant vigor | Strong | Strong to very strong | Strong | Medium |
| Fruit size | Large | Large to very large | Large | Medium to large |
| Fruit acidity | Medium to high | Low to medium | Medium | Low |

BRIEF DESCRIPTION OF THE DRAWINGS

The accompanying drawings are color photographs of the new blueberry plant 'NS 14-7' during the third year of growth under the ecological conditions prevailing at the breeder's property, which is located at Yanchep Springs in Yanchep, Western Australia.

Figure 1:
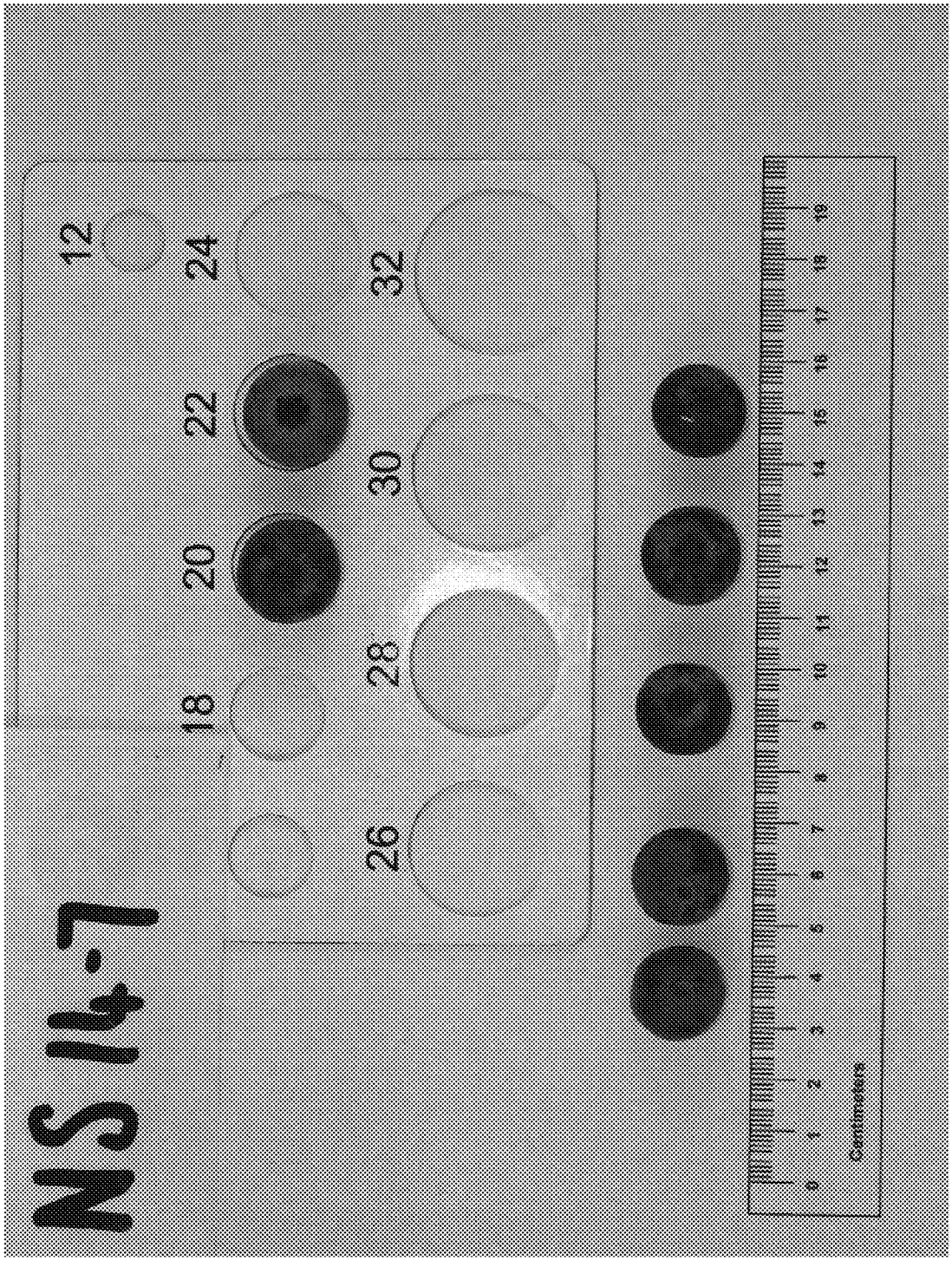
FIG. 1 is a color photograph, which shows fruit of the new blueberry plant 'NS 14-7', the fruit being sufficiently mature for harvesting and shipment. This photograph also depicts the large fruit size and the color of the ripe fruit.
Figure 2:
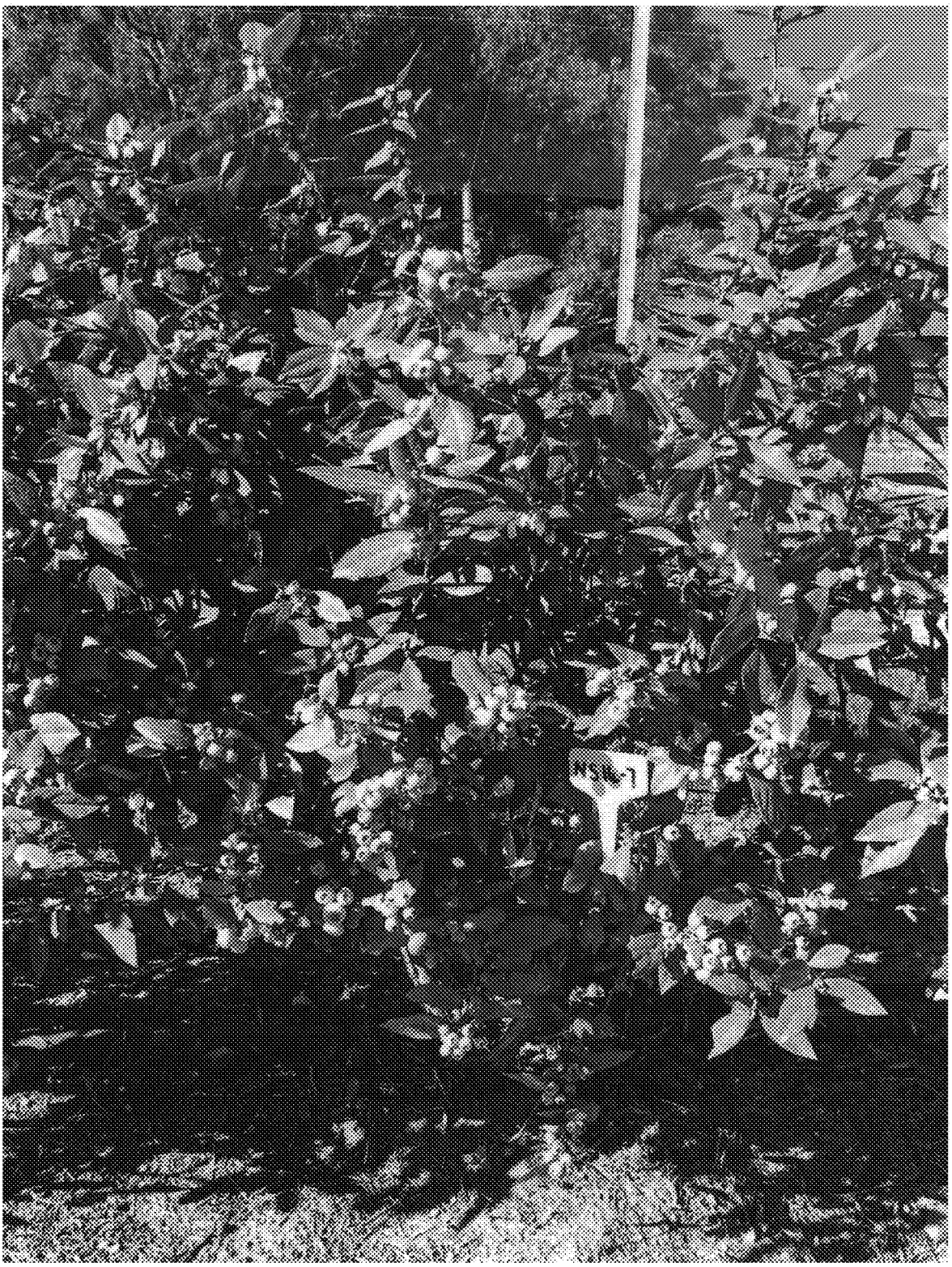
FIG. 2 is a color photograph, which shows the new blueberry plant 'NS 14-7'. This photograph depicts a mature bush with ripe and unripe fruits, the large fruit size, and the upright to semi-upright growth habit of the bush. The ripe fruit is sufficiently mature for harvesting and shipment.
Figure 3:
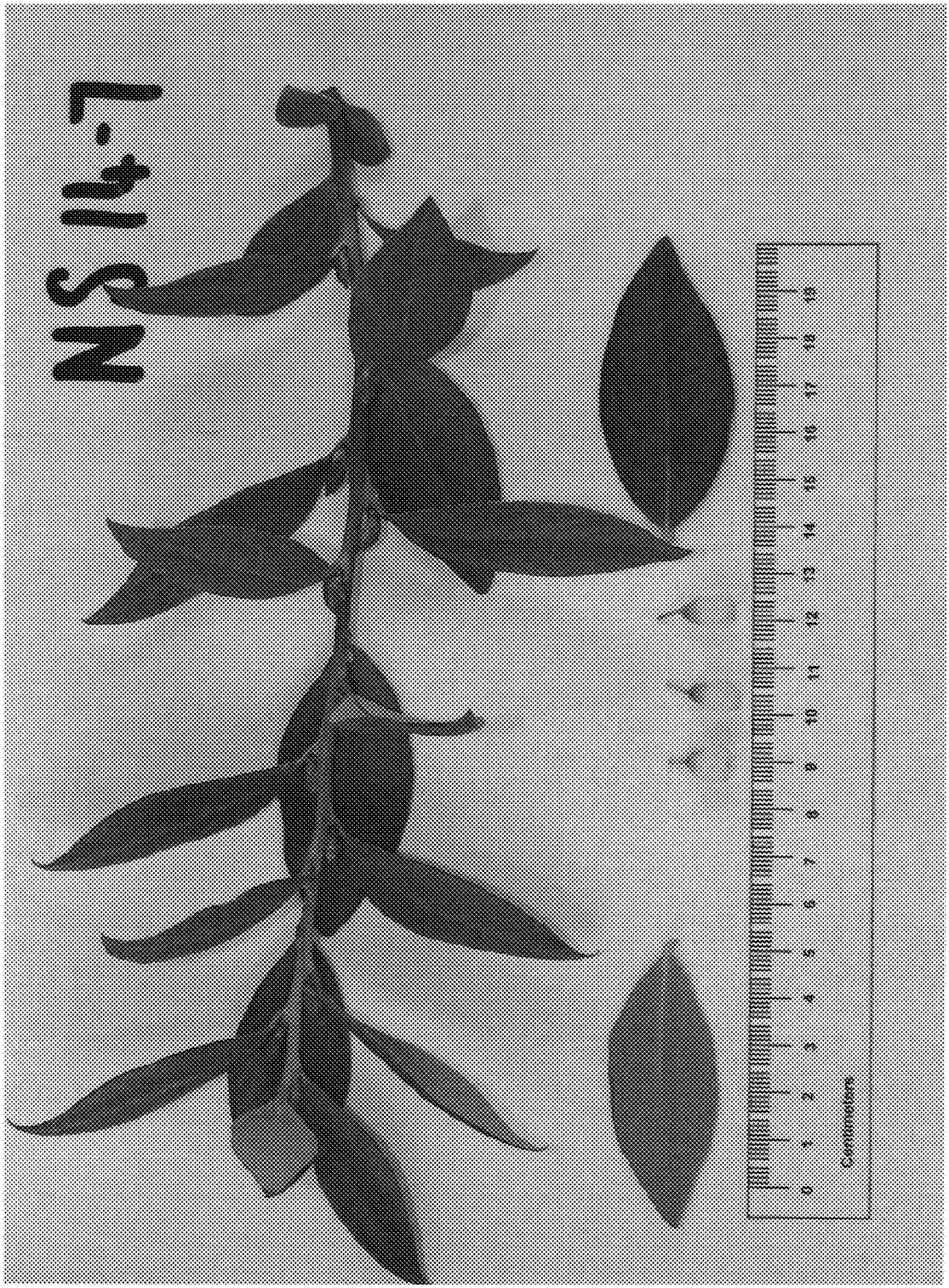
FIG. 3 is a color photograph, which shows a portion of a vegetative stem bearing leaves of the new blueberry plant 'NS 14-7'. This photograph depicts leaves at different stages of maturation, the upper and under side coloration thereof, and three blooms.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition, hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the third year of growth under the ecological conditions prevailing at the breeder's property, which is located at Yanchep Springs in Yanchep, Western Australia.

Plant: General.

*Vigor.*—Considered strong for the species. This is comparable to the seed parent '8-10', wherein the plant vigor is also considered strong. This is in contrast to the pollen parent 'EB 8-30', wherein the plant vigor is only considered medium. This is further in contrast to the closest known variety 'EB 9-2', wherein the plant vigor is considered strong to very strong.

*Growth habit.*—Considered upright to semi-upright. This is in comparison to the commercial variety 'Ivanhoe' (unpatented), which is considered to be upright, and the commercial variety 'Bluetta' (unpatented), which is considered to be semi-upright.

*Average size of plant.*—1.20 meters in height by 1.05 meter in width.

*Internode length* (*space between nodes*).—Considered short to medium, 14-15 millimeters (mm).

*Bark color.*—RHS Grey Reddish Orange Group 177C.

*Color, one year old shoots.*—RHS Strong Yellow Green Group 141C.

*Fruiting type.*—On one-year-old shoots only, in like manner to commercial varieties 'Darrow' (unpatented) and 'Patriot' (unpatented).

Foliage: General.

*Average leaf length.*—Considered long for the species, 63.5 mm.

*Average leaf width.*—Considered medium for the species, 26.7 mm.

*Color of leaf upper.*—RHS Moderate Olive Green Group 147A.

*Color of leaf underside.*—RHS Greyish Yellow Green Group 148C.

*Vein color of plant leaf.*—RHS Moderate Yellow Green Group 146B.
*Venation pattern of leaf.*—Pinnate reticulate.
*Leaf apex texture.*—Glabrous.
*Leaf apex shape.*—Acute.
*Leaf base shape.*—Acute.
*Leaf shape.*—Elliptic.
*Leaf margin.*—Entire or serrate — Entire.
*Leaf arrangement of plant.*—Alternate.

Flowers:

*Number of flowers per inflorescence.*—10 to 12.
*Average length of inflorescence (excluding peduncle).*—Considered very short to short, 7.1 mm.
*Corolla shape.*—Urceolate.
*Corolla tube surface texture.*—Ridges are present on the corolla tube.
*Average corolla size.*—Considered medium, 7 to 8 mm in length by 7 mm in width.
*Corolla diameter.*—7.34 mm.
*Average corolla aperture size.*—3.03 mm.
*Corolla color.*—RHS White Group NN155D.
*Pedicel color.*—RHS Brilliant Green Group 149C.
*Average pedicel length.*—4.36 mm.
*Average calyx diameter.*—Considered medium, 6.0 mm.
*Average calyx basin depth.*—Considered deep, 3.16 mm.
*Attitude of sepals.*—Considered erect.
*Type of sepals.*—Considered reflexed.

Reproductive organs:

*Average size of pollen anthers.*—5.89 mm.
*Color of pollen anthers.*—RHS Moderate Orange Group 170B.
*Average pistil length.*—8.27 mm.
*Pistil color.*—RHS Strong Yellow Green Group 145A.

Fruit:

*Color of unripe fruit.*—RHS Strong Yellow Green Group 144B.
*Color of fruit skin.*—RHS Bluish Black Group 203C, also considered "dark blue" in like color to the commercial variety 'Heerma' (unpatented), after removal of bloom.
*Color of ripe fruit flesh.*—RHS Light Yellow Green Group 145B.
*Color of seeds.*—RHS Strong Orange Yellow Group 163B.
*Average fruit size.*—Considered large, 18 to 19 mm in diameter and 16.34 mm in height. This is comparable to the seed parent '8-10', wherein the fruit size is also considered large. This is in contrast to the pollen parent 'EB 8-30', wherein the fruit size is considered medium to large. This is also in contrast to the closest known variety 'EB 9-2', wherein the fruit size is considered large to very large.
*Average weight of fruit.*—2.5 grams.
*Average fruit production.*—6-8 kilograms on a three-year-old bush.
*Berry shape.*—Considered round.
*Sweetness when ripe.*—Considered medium for the species.
*Firmness when ripe.*—Considered medium for the species.
*Acidity when ripe.*—Considered medium to high for the species. This is in contrast to the seed parent '8-10', wherein the fruit acidity is considered medium. This is also in contrast to the pollen parent 'EB 8-30', wherein the fruit acidity is considered low. This is further in contrast to the closest known variety 'EB 9-2', wherein the fruit acidity is considered low to medium.
*Cluster density.*—Considered medium to dense for the species.
*Storability of fruit.*—Considered excellent for the species.
*Market use of fruit.*—1st grade fresh market fruit.
*Date of bud burst.*—This variety is evergreen, effectively with buds, flowers, and fruit throughout the whole of the year under the ecological conditions prevailing in Yanchep, Western Australia.
*Date of vegetative bud burst.*—August under the ecological conditions prevailing in Yanchep, Western Australia.
*Date of bloom time.*—May under the ecological conditions prevailing in Yanchep, Western Australia, also considered early on one-year old shoot in like manner to the commercial variety 'Weymouth' (unpatented).
*Duration of bloom time and bloom intensity.*—10 weeks; bloom intensity is considered strong.
*Beginning of fruit ripening.*—Considered early on one-year-old shoot in like manner to the commercial variety 'Blueray' (unpatented).
*First pick date.*—August under the ecological conditions prevailing in Yanchep, Western Australia.
*Last pick date.*—November under the ecological conditions prevailing in Yanchep, Western Australia.
*Pollination requirements.*—Self-fertile.
*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a plant letters patent is:

1. A new and distinct variety of blueberry plant, substantially as illustrated and described, which is characterized principally as to novelty by a strong vigor and by producing fruit considered large in size and medium to high in acidity under the ecological conditions prevailing in Yanchep, Western Australia.

* * * * *